(12) United States Patent
Bruggeman et al.

(10) Patent No.: US 7,297,359 B2
(45) Date of Patent: Nov. 20, 2007

(54) PROCESS FOR THE PREPARATION OF A FOAMED PRODUCT AND PRODUCTS OBTAINABLE BY THIS PROCESS

(75) Inventors: Yvonne Evelien Bruggeman, Vlaardingen (NL); Peter Ravestein, Vlaardingen (NL)

(73) Assignee: Conopco, Inc., Edgewater, NJ (US)

( * ) Notice: Subject to any disclaimer, the term of this patent is extended or adjusted under 35 U.S.C. 154(b) by 505 days.

(21) Appl. No.: 10/471,482

(22) PCT Filed: Feb. 6, 2002

(86) PCT No.: PCT/EP02/01212

§ 371 (c)(1),
(2), (4) Date: Aug. 25, 2003

(87) PCT Pub. No.: WO02/071870

PCT Pub. Date: Aug. 19, 2002

(65) Prior Publication Data

US 2004/0069158 A1    Apr. 15, 2004

(51) Int. Cl.
*A23L 1/0524* (2006.01)
*A23G 9/20* (2006.01)
(52) U.S. Cl. .......................... 426/564; 426/565; 426/570
(58) Field of Classification Search ................ 426/564, 426/565, 570
See application file for complete search history.

(56) References Cited

U.S. PATENT DOCUMENTS

| 4,292,972 A | * | 10/1981 | Pawelchak et al. | 604/368 |
|---|---|---|---|---|
| 4,505,943 A | * | 3/1985 | Dell et al. | 426/565 |
| 4,510,166 A | | 4/1985 | Lenchin et al. | |
| 5,384,145 A | | 1/1995 | Gonsalves et al. | |
| 5,384,146 A | * | 1/1995 | Gonsalves et al. | 426/565 |
| 6,372,280 B1 | * | 4/2002 | Gonsalves et al. | 426/564 |
| 2002/0142992 A1 | * | 10/2002 | Scherr | 514/54 |

FOREIGN PATENT DOCUMENTS

| EP | 0 426 434 | 5/1991 |
|---|---|---|
| WO | 94/17137 | 8/1994 |
| WO | 96/03440 | 2/1996 |
| WO | 98/22513 | 5/1998 |
| WO | 99/11672 | 3/1999 |
| WO | 00/40098 | 7/2000 |

OTHER PUBLICATIONS

Int'l. Search Report No. PCT/EP 02/01212 dated Jul. 29, 2002—4 pp.

* cited by examiner

*Primary Examiner*—C. Sayala
(74) *Attorney, Agent, or Firm*—Michael P. Aronson

(57) ABSTRACT

Foamed products based on an aqueous composition comprising an oxidised ferulyated polymer are stable both during storage and after freezing and subsequent storage. A process for preparing these products is provided.

12 Claims, No Drawings

PROCESS FOR THE PREPARATION OF A FOAMED PRODUCT AND PRODUCTS OBTAINABLE BY THIS PROCESS

FIELD OF THE INVENTION

The invention relates to a formulation and process for providing foamed products which are freeze-thaw stable and also storage stable.

BACKGROUND OF THE INVENTION

The object of providing a freeze-thaw stable foam which is also storage stable has been addressed in the art.

U.S. Pat. No. 5,384,145 relates to a whipped topping based on an aqueous solution of whey protein isolate or concentrate which has a low fat content of from 8% to 15% and has an overrun in excess of 250%, which is freeze-thaw stable and refrigerator stable for 21 days and shows good whippability.

However these compositions are not stable if oil is not included in their composition. Furthermore the gas phase in these products is believed to be stabilised by non-covalent, physical bonding of whey protein on the gas/liquid interphase which is mainly due to protein denaturation. These interactions are non covalent and hence do not provide desired long term stability of the foam.

Furthermore foamed products based on egg white are widely known. However, egg white based foam is not freeze-thaw stable and not very firm.

WO-A-00/40098 discloses crosslinked pectin which is dried and as such added to an ice cream formulation. The obtained products were found to have a sol-like character meaning that it is like a dispersion of gelled particles in a liquid, and did not maintain their shape upon storage at room temperature for 30 minutes or more. Under these storage conditions the products collapsed.

Hence it is an object of the invention to provide a foamed product which is freeze-thaw stable, and shows a creamy, tasteless and soft mouthfeel. Preferably these products are firm and they preferably retain their shape during storage.

SUMMARY OF THE INVENTION

It has surprisingly been found that these features can be fulfilled by a foamed composition comprising water and an oxidised ferulyolated compound prepared in a process wherein the oxidation is carried out during or after foam formation.

Therefore the invention relates to a process for the preparation of a foamed product comprising the steps of:
 a) providing a mixture of a liquid and a ferulyolated compound
 b) incorporating a gas phase in this mixture
 c) combining said mixture with an oxidant capable of oxidation of the ferulic acid groups in the ferulyolated compound, preferably under conditions wherein homogeneous distribution of the oxidant in the liquid is ensured.

In a further aspect the invention relates to a foamed product comprising a dispersed gas phase and a liquid phase comprising an oxidised ferulyolated compound in an amount of from 1 to 20 wt % on total weight of the liquid phase, obtainable by the above process.

In a further aspect the invention relates to food products comprising these foamed products.

DETAILED DESCRIPTION

For the purpose of the invention a foam is defined as an emulsion-like two phase system where gas bubbles are dispersed in a (sometimes relatively small) volume of liquid containing surface active molecules, preferably macromolecules. A foam can for example be formed by whipping air into an aqueous composition comprising egg white.

The foams according to the invention optionally contain an oil, preferably a triglyceride oil, as a second dispersed phase. These products may show a more mousse like structure which is more dense than a common foam structure. However these products are also encompassed in the invention.

Foams in the context of the invention differ from products with a gel structure as these latter structures only comprise gas dissolved in the liquid from which the gel is derived. The current foam products comprise more gas than this level, which is determined merely by the solubility of gas in the liquid from which the gel is derived.

Tasteless in the context of the invention means that the foamed products have a bland taste unless flavour compositions are added. This bland taste is desired as it enables use of the foams in any type of product.

In the context of the invention, the terms "fat" and "oil" are used interchangeably. The term oil encompasses both triglyceride oils and diglyceride oils.

For the purpose of the current invention, wt % is defined as weight percent on total weight of the liquid phase of the foamed product, unless otherwise is indicated. In this calculation, the liquid phase is considered to comprise all water soluble and water dispersible ingredients and all oil or ingredients that can be dissolved or dispersed therein.

The term oxidant is used to indicate an oxidising agent, which can be either a chemical oxidising agent or an enzyme. An enzyme can be used alone or in combination with a co-oxidant such as hydrogen peroxide.

The invention regards a process to prepare a foamed product, on the basis of compounds containing ferulic acid groups. Care should be taken that the conditions are such that the desired specific volume and firmness are reached. Especially the oxidation of the ferulic acid units should be carefully controlled.

It is known that oxidation of a ferulyolated compound under quiescent conditions leads to the formation of a gel. Reference is made to WO-A-96/03440 and WO-A-98/22513. Hence in the absence of any other measures, the blending of ferulyolated compound and an oxidant which is sufficiently powerful to enable oxidation of the ferulic acid units, will lead to the formation of a gel.

It has surprisingly been found that if a gas phase is incorporated in a liquid comprising a ferulyolated compound, under simultaneous oxidation and/or followed by oxidation, a foamed product results which is freeze-thaw stable, storage stable and shows the desired taste and mouth feel upon consumption.

Therefore in one aspect the invention relates to a process for the preparation of a foamed product comprising the steps of:
 a) providing a mixture of a liquid and a ferulyolated compound,
 b) incorporating a gas phase in this mixture
 c) combining said mixture with an oxidant capable of oxidation of the ferulic acid groups in the ferulyolated compound, preferably under conditions wherein homogeneous distribution of the oxidant in the liquid is ensured.

Without wishing to be bound by any theory, applicants believe that the oxidised ferulyolated compound acts as a surfactant and absorbs at the gas/liquid interface. In this way the ferulyolated compounds are believed to be responsible for the tendency of the liquid to foam and to impart stability to the resulting foamed product. The cross linking of the ferulic acid units by oxidation is believed to fix the structure of a dispersed gas phase in a matrix of ferulyolated compounds, thereby increasing the stability of the foamed product, both in terms of storage stability and in terms of freeze-thaw stability.

The process according to the invention comprises in step (b) a step wherein a gas phase is incorporated into the mixture. This gas incorporation leads to the formation of a foam type structure.

The foam type structure is prone to decline and/or collapse unless step (c) is carried out. As explained above, it is believed that in step (c) the foam structure is fixed by the covalent bonds which arise from oxidation of the ferulic acid groups. Step (c) is the oxidation of ferulic acid groups. To prevent collapse of the formed foam structure, it is desired that step (c) is carried out within a short time frame, preferably in the order of seconds to at most a few minutes. Suitable conditions to obtain this fast formation of an oxidised structure are exemplified below. Step (c) may be carried out simultaneously with the incorporation of gas in step (b) or after the gas has been incorporated. Step (c) is preferably carried out after step (b). If the oxidation is carried out simultaneously, the oxidant is preferably added towards the end of step (b) when at least part of the gas has been incorporated, preferably at least 50 vol % of the gas has been incorporated.

Step (c) regards the combining of the preferably foamed mixture with an oxidant to obtain oxidation of ferulic acid groups. This combining may be carried out actively as an addition of oxidant to the mixture of step (b). Alternatively the combining may result from the formation in situ of the oxidant in the mixture of step (b). In situ generation of the oxidant may for example be mediated by the action of glucose oxidase, forming hydrogenperoxide as a reaction product. Hydrogen peroxide is thus combined into the mixture.

The gas can be any gas, but is preferably selected from the group consisting of air, nitrogen, carbon dioxide and ammonia gas.

The gas can be incorporated by any suitable method. Preferably the gas phase is incorporated by a method selected from the group consisting of subjecting the mixture to high shear treatment, addition of a leavening system under conditions where leavening takes place, and addition of an enzymatic system which leads to gas formation.

If gas is incorporated by a shear treatment, said shear treatment in step (b) is preferably a high shear treatment. For the purpose of the invention shear is defined as a strain resulting from applied forces that cause or tend to cause contiguous parts of a body to slide relatively to each other in a direction parallel to their plane of contact.

It has been found that gentle shaking of a product does not lead to formation of a foam, nor does gentle mixing of the two components with a fork. Use of a home mixer at the lowest speed may lead to the formation of a foam but this will have a small overrun only.

For the purpose of the invention overrun is defined as the increase in volume of a product over the volume of the mix due to the incorporation of gas. For further information on overrun reference is made to Marshall et al 1996 in "Ice Cream".

Examples of suitable apparatus to impart shear are a turrax™, a Hobart™ at high speed, and a scraped surface heat exchanger. Further guidance on high shear treatment is provided in the examples.

Preferably these apparatus are used at at least half of their maximum stirring speed to obtain a foamed product.

Preferably the shear treatment in step (b) continues for some time to increase the specific volume of the liquid to produce a foam. Preferably the shear is applied until the specific volume of the foam reaches its maximum value. The total amount of time during which shear is applied is preferably from 1 second to several minutes, more preferred from 2 seconds up to 5 minutes, most preferred from 5 seconds up to 1 minute. As a guideline it is preferred that the shear treatment is stopped once the foam has been formed and does not increase visibly in volume anymore. This can be determined quantitatively by determination of the specific volume versus time. Generally a larger volume of starting liquid requires a longer shear treatment before the maximum specific volume for the system is obtained. A skilled person will understand that the time during which shear is applied, among others also depends on the shear rate.

According to another embodiment, gas is incorporated by use of a leavening salt. Suitable leavening systems are for example described in Cereal Foods World, 41, pages 114-116, 1996 and include yeast fermentation or chemical leavening systems.

Preferably the leavening agent included in the leavening system is selected from the group of sodium bicarbonate, potassium bicarbonate, ammonium bicarbonate and disodiumpyrophosphate.

Alternatively gas is incorporated by addition of an enzymatic system generating a gas. A suitable example of such a system is the combination of a catalase and hydrogen peroxide as substrate, which will lead to the formation of oxygen gas.

The amount of gas that is included in a volume of liquid determines the specific volume of a foamed product. The foamed products according to the invention preferably show a specific volume between about 0.01 to 0.9 g/ml, more preferred 0.1 to 0.7 g/ml. The method to determine specific volume is described in the examples.

Shear is preferably applied during mixing of the ferulyolated compound and the oxidant in step (c). Preferably the oxidant is added to the gas phase containing mixture.

The shear applied in this step may be low or high shear as long as the shear treatment ensures that the oxidant is preferably distributed homogeneously in the liquid. If the distribution is not homogeneous, only local oxidation may result and other parts of the liquid may not be oxidised and hence will not structure the foam.

After the incorporation of a gas in step (b) and after blending of the oxidant, preferably the foamed product is left to stand for some time, preferably 10 seconds to 1 minute to ensure that oxidation of the ferulic acid groups can take place to fix the foam that has been formed in step (b).

In a preferred process, the temperature during mixing in step (a) is between 10 and 40° C.

The temperature in step (b) can be any suitable temperature. A temperature between −20 and 40° C., preferably from 4 to 20° C. is preferred.

The foamed product is preferably stored at a temperature below 25° C., more preferred from −20 to 25° C.

Storage at increased temperature of about 50 to 90° C. is possible but was found to lead to a dried structure. After such a drying treatment at increased temperature, a brittle foam results. This structure resembles the structure of a meringue. In a further aspect the process includes this drying step.

The oxidation may be accomplished by the action of a powerful chemical oxidant such as potassium periodate, potassium permanganate, or potassium ferricyanide.

Alternatively the oxidation can be accomplished by use of an oxidising enzyme such as a peroxidase, a polyphenol oxidase e.g. catechol oxidase, tyrosinase, or a laccase.

Peroxidases can be divided into those originating from plants, fungi or bacteria and those originating from a mammalian source such as myeloperoxidase and lactoperoxidase (LPO).

Laccases are obtainable from a variety of microbial sources notably bacteria and fungi (including filamentous fungi and yeasts), and suitable examples of laccases include those obtainable from strains of *Aspergillus, Neurospora* (e.g. *N. crassa*), *Prodospora, Botrytis, Collybia, Fomes, Lentinus, Pleurotus, Trametes* [some species/strains of which are known by various names and/or have previously been classified within other genera], *Polyporus, Rhizoctonia, Coprinus, Psatyrella, Myceliophtora, Schytalidium, Phlebia* or *Coriolus*.

Preferred enzymes are selected from the group comprising horseradish peroxidase, soy bean peroxidase, *Arthromyces ramosus* peroxidase and laccases that show a redox potential of preferably more than 550 mV as described in E. Solomon et al, Chem Rev, 1996, p 2563-2605.

The extent of oxidation of the ferulyolated compound can be measured by spectrophotometric determination of the absorbance at 375 nm. Absorption at this wavelength is characteristic for an oxidised ferulic acid group.

In case a chemical oxidant is applied, the oxidant is preferably added in the form of a diluted aqueous solution.

In case an enzymatic oxidising system is applied, the enzyme is preferably added in the form of a solution or a dispersion in an aqueous buffer system. The enzymes cited above are suitable enzymes. Some enzymes, such as peroxidases require the presence of a co-oxidant such as hydrogen peroxide for their activity. The co-oxidant is preferably added separately from the enzyme that requires it's presence.

The amount of enzyme added is expressed in terms of activity units. Preferably enzyme is present in excess. The amount of enzyme added is preferably such that fast gelation occurs to immediately fix the foam structure created in step (b). For a peroxidase the amount of enzyme added is preferably from 50 to 10.000 units ABTS activity per ml of liquid.

The gas incorporation in step (b) and oxidation in step (c) can be carried out at any temperature, e.g. between −20° C. and 40° C., preferably from 20 to 40° C. If the oxidation is carried out enzymatically, the temperature during step (b)-(c) is preferably from 20 to 40° C. However also lower temperature are possible provided the enzyme shows activity at this temperature. Therefore most preferred the temperature is around the temperature at which the enzyme shows maximum activity.

Optionally oil or fat is included in the foam product. The oils and fats as listed above can suitably be included.

The oil or fat is preferably added between step (a) and (b) or during the incorporation of gas in step (b).

It is preferred that the oil or fat is added to the water phase to form a water continuous liquid instead of the reversed order whereby a fat continuous system is formed.

In a further aspect the invention relates to a foamed product comprising a dispersed gas phase and a liquid phase comprising an oxidised ferulyolated compound in an amount of from 1 to 20 wt % on total weight of the liquid phase, obtainable by the above process.

The preferred ingredients/liquid composition as outlined below equally apply to the foamed products as prepared according to the above process.

The foamed products according to the invention are freeze-thaw stable. In the context of the invention this implies that after storage at at least −20° C. for a period of at least 2 hours, and subsequent thawing at room temperature (about 25° C.), the products are characterized by a specific volume which is 70 to 100% of the specific volume of the foamed product before it was stored at at least −20° C.

The foamed products according to the invention are also storage stable. This means that the foamed product when stored at a temperature of from 4 to 25° C. for at least 7 days shows a specific volume which is at least 70 to 100% of the specific volume before storage. Furthermore storage stable products preferably do not show an off flavour upon storage. Flavour/taste and colour characteristics are determined by a panel test.

In a further aspect the invention relates to a foamed product comprising a dispersed gas phase and a liquid phase comprising an oxidised ferulyolated compound in an amount of from 1 wt % to 20 wt % on total weight of the liquid phase, said product being stable at ambient temperature.

A first insight in freeze-thaw stability and storage stability of foams can be obtained by visual inspection of the thawed products. Foams which collapse or show a strong volume decline and/or substantial water release are not stable in the context of the invention.

The foamed products according to the invention are firm which means they show a hardness value of at least 0.5 g, more preferred from 0.5 to 25 g, even more preferred from 8 g to 24 g, at room temperature (about 25° C.) under the measurement conditions indicated in the examples.

Preferably freeze-thaw stable foams show a difference in hardness value of at most 20% compared to the hardness value before they were frozen and thawed under the conditions specified above.

According to a further aspect stable products (both with respect to storage stability and freeze-thaw stability) do not show water release after the respective treatments. Water release is often seen on foam type products or emulsions and is referred to as syneresis.

The method to determine water release is described in the examples. Preferred products show a water release of less than 0.2 ml/g determined by the method according to the examples.

More preferably the foams according to the invention show substantially no water release after storage or after a freeze-thaw treatment as specified above.

Examples of foamed products are whipped toppings, whipped cream, foamed shaving cream.

The foamed product comprises an oxidised ferulyolated compound in the liquid phase. Ferulic acid groups (4-hydroxy-3-methoxy-cinnamyl—groups) are known to be capable of crosslinking in the presence of certain oxidants (e.g. Oosterveld et al; oxidative crosslinking of pectic polysaccharides from sugar beet pulp, Carbohydrate research 328; 199-207, 2000). In the oxidation process a new covalent bond is formed between two individual ferulic acid groups.

The compound comprising oxidised ferulyolated groups is preferably a polymer, more preferred a polysaccharide. Examples of suitable polymers include pectin, arabinan, galactan, cellulose derivatives, galactomannans such as guar gum, locust bean gum, starches or other polymers comprising hydroxyl groups which can be esterified to a ferulic acid group.

The polymers comprising ferulic acid groups can be naturally occurring or synthesised polymers. Examples of naturally occurring polymers with ferulic acid groups are sugar beet pectin and arabinoxylanes isolated from cereals.

Synthetic processes to prepare polymers with ferulic acid groups generally include esterification of ferulic acid to a free hydroxyl group situated on the polymer backbone or on a sugar substituent.

In a highly preferred embodiment, the foamed product comprises an oxidised pectin, even more preferred oxidised sugar beet pectin. The principal building units of pectin are smooth homogalacturonic regions and rhamnified hairy regions in which most neutral sugars are located. Arabinose is the predominant neutral sugar. Galactose is present in rhamnogalacturonan. 50-55% of the ferulic acid groups are linked to arabinose units and about 45-50% of the ferulic acid groups are linked to galactose residues.

Preferably 15 to 80% of all ferulic acid groups are oxidised in the final foamed product.

It is preferred that the majority of ferulic acid groups is not oxidised before gas is incorporated in step (b). More preferred before step (b) at most 10% of all ferulic acid groups are oxidised.

The amount of oxidised ferulyolated compound in the liquid phase of the foamed product is from 1 to 20 wt %. Lower amounts were found not to provide sufficient firmness and storage stability was unsatisfactory. Higher amounts often do not dissolve at a satisfactory level and may lead to inclusion of the oxidant by oxidised polymers. This may inactivate the oxidant and may lead to phase separation.

Preferably the amount of oxidised ferulyolated compound is from 1 to 10 wt %, more preferred 1 to 4 wt %, even more preferred from 2 to 4 wt % on total liquid phase.

The liquid phase can be any liquid phase, but the presence of at least some water is required.

In a highly preferred embodiment, the liquid phase comprises water in an amount of at least 20 wt % on total weight of the liquid phase.

Examples of liquid phases which fulfil this requirement are milk, cream, juices and certain oil in water and water in oil emulsions.

These liquid phases are preferred for the product according to the invention.

Optionally the liquid phase comprises an organic solvent such as ethanol.

Although the protein based foams as described in the prior art were as such found to be unstable upon freezing and thawing, the current products may comprise some protein. Protein may serve to improve their nutritional value, their taste and appearance and foam volume especially if the foam is prepared at relatively low shear.

However care should be taken that the amount of protein is not too high, which was found to lead to products which do not show the desired freeze-thaw stability.

Therefore the foamed product preferably comprises protein in an amount from 0.1 to 15 wt %, more preferred from 1 to 10 wt %, even more preferred from 2 to 5 wt %, on total weight of the liquid phase.

Suitable proteins include whey protein, egg white protein, casein, other milk protein, soy protein, potato protein, rice protein, shea protein, maize protein, barley protein or a combination thereof.

In a highly preferred embodiment the products according to the invention comprise a protein in an amount from 1 to 5 wt % and a ferulyolated pectin in an amount from 1 to 4 wt %.

It is well known that fat present in an aqueous egg white composition prevents the whippability of the composition to a great extent. It has surprisingly been found that the current foams are stable and show the desired specific volume, even in the presence of oil or fat. It has been found that amounts of fat or oil up to 60 wt % on the liquid phase volume are tolerable and do not severely reduce the foam firmness or its stability. Compared to a foam based only on ferulyolated compound, without fat or oil, the compositions that contain oil or fat show a more creamy, mousse-like structure with less overrun. For products comprising oil or fat the specific volume is preferably from 0.01 to 0.9 g/ml, preferably 0.1 to 0.9 g/ml.

The oil or fat is preferably selected from the group comprising sunflower oil, coconut oil, butter fat, rapeseed oil, olive oil, peanut oil or oils extracted from plant or flower material such as rose oil, and combinations thereof. Also fractionated oils are encompassed in the invention.

The foamed product may optionally comprise further ingredients such as salt, flavour components, colourants, emulsifiers, acidifying agents, (co)-oxidants such as hydrogen peroxide, and the like. If particulate ingredients such as fruit pieces or nuts are added, it is preferred that these are added shortly after the desired specific volume has been reached and while oxidation is at least ongoing. This is preferred because the particulate ingredients are then likely to be enclosed in the oxidised crosslinked network, which improves the stability of the final foamed product and reduces the tendency of the particulate ingredients to precipitate on the bottom of a jar containing the foamed product.

In a further aspect the invention relates to a food product comprising a foamed product according to the invention. Examples of food products which suitably may incorporate the foamed product include ice cream, margarine, table spreads, butter, desserts, and yoghurt.

The invention is especially suitable for ice cream, milk ices and water ice products. Water ice, milk ice and ice cream will be referred to as frozen confection hereafter. Such products and processes to prepare these are for example disclosed in "Ice Cream" by R. T. Marshall & W. S. Arbuckle, $5^{th}$ Edition, 1996, Chapman & Hall, New York.

A frozen confection is a foamed, sweet product containing a large amount of ice. Frozen confections generally comprise sugars and sweeteners (such as sucrose and glucose), water and optionally ingredients selected from the group comprising protein, fat, thickeners, emulsifiers and stabilisers. Furthermore taste and flavour components or preservatives are optionally included.

Water ice and milk ice are generally fat-free whereas ice cream preferably comprises from 2 to 20% fat. The overrun of frozen confections is preferably from 30 to 150%. The preferred overrun among others depends on the type of ice product. The overrun for water ice is generally lower than for ice cream.

In this preferred aspect a process is provided for preparing a frozen confection wherein a) a mixture of ingredients of the frozen confection and a ferulyolated compound in water is prepared at a preferred temperature of from 15 to 60° C.

b) a gas phase is incorporated in this mixture c) the mixture is mixed with an oxidant capable of oxidation of the ferulic acid groups in the ferulyolated compound, preferably under conditions wherein homogeneous distribution of the oxidant in the liquid is ensured d) the foam which results from step (c) is frozen at a temperature below minus 4° C., preferably from −50 to −10° C.

The mixture of step (a) is preferably a homogeneous mixture of the ingredients in the frozen confection. The ingredients are described below.

In step (c) ferulic acid groups are linked by oxidation. This is carried out simultaneously with gas incorporation or more preferred after incorporation of gas in step (b).

Preferably the oxidation in step (c) is continued for some time, preferably in the order of 1-10 minutes, to allow the product to reach maximum stability. Hence it is preferred that freezing is not done immediately after step (c) but after the foamed mixture has been allowed to stand for at least about 1 minute.

Optionally a homogenisation and/or pasteurisation and/or sterilisation step is included before step (b).

The temperature during step (b) and (c) can be any suitable temperature. A temperature from (minus) −20° C. to +15° C., preferably from −15° C. to +5° C. is preferred. Optionally the product is already partly frozen before step (d).

The preferred characteristics of the foamed product described above equally apply to the process for preparing a frozen confection.

In a further aspect the invention relates to a frozen confection, preferably ice cream obtainable by this process.

The preferred ferulyolated compound is (sugar beet) pectin, preferably in an amount of from 0.8 to 5 wt %, more preferred from 1 to 4 wt % on total weight of the frozen confection.

Ice cream preferably comprises about 2 to 7 wt % protein which are usually added as part of whey powder or skim milk powder. Common sweeteners that are optionally included are preferably selected from the group comprising sucrose, glucose, lactose, corn syrups or a combination thereof.

Stabilisers are preferably selected from the group comprising guar gum, locust been gum, carrageenan, starch, gelatin or a combination thereof. Preferred amount is from 0.1 to 1 wt % on product.

Preferred emulsifiers are selected from the group comprising saturated monoglycerides, saturated diglycerides of fatty acids, polyglycerol esters, sorbitan esters, stearoyl lactylate, lactic acid esters, citric acid esters, acetyllated monoglyceride, diacetyl tartaric acid esters, polyoxyethylene sorbitan esters, lecithin, egg yolk, or a combination thereof. Preferred amount is from 0.05 to 0.5 wt % on product.

Optionally the frozen confection comprises colour or flavour components. A well known flavour component for ice cream is for example vanillin. Care should be taken that vanillin is preferably added after the oxidation in step (c) has been completed because of the structural similarity of ferulic acid and vanillin. Addition of vanillin before oxidation may perturb the oxidation reaction. Alternatively the vanillin level is sufficiently low compared to the amount of ferulyolated compound such that the oxidation reaction is not disturbed. It was further found that the presence of fat in which vanillin easily dissolves, may reduce any negative influence of vanillin on the oxidation of ferulic acid residues.

The stability of these ice confections is preferably determined by a so called meltdown test which is described in the examples.

In an alternative embodiment, the invention relates to creamy or pastey products comprising the foamed product. Examples of such products include shaving cream and skin cream.

The invention is illustrated by the following examples.

EXAMPLES

General Techniques That Were Applied

1. Measurement of Hardness
   Apparatus used: Texture Analyser model LFRA 1000 g/100 g from CNC Farnell. Unit 1 Manor place Manor Way, Boreham Woods, Herts, UK.
   Probe used: probe made of synthetic material, probe size: diameter 25 mm, height 35 mm.
   Settings of the Texture analyser:
   Penetration speed: 2 mm/sec
   Distance: 10 mm The hardness value is determined in grams.

The temperature is 25° C.

2. Determination of Specific Volume (S.V.)

The specific volume of the foamed product was measured by filling a calibrated cup with known volume and weight and leveling the top. The weight of the filled cup was measured. SV is the ratio between the volume of the foamed product in the cup and the weight of the foamed product in the cup expressed as g/ml.

3. Determination of Water Release

Calibrated 50 ml tubes were completely filled with foam. Water release (water layer on bottom of tube) was determined. The weight of the foam was determined by weighing the empty and the filled tube. Water release is expressed as ml water released per gram of foam.

4. Activity Assay

Add 100 µl 20 mM ABTS (2,2'-azino-bis(3-ethylbenzothiazoline-6-sulfonic acid (ABTS) stock solution made in indicated buffer) to 880 µl 25 mM phosphate buffer, pH 6.0. Incubate for 5' at 30° C. Add 10 µl 100 mM hydrogen peroxide. Start the reaction by addition of 10 µl enzyme (diluted in such a way that a linear curve could be measured). Measure the formation of ABTS radical at 414 nm using a spectrophotometer.

Specific activity is defined as: µmol ABTS oxidised per minute per mg protein at pH 6.

Example 1-2

Materials:
12.5 wt % egg white solution (prepared from High-Whip powder, van Enthoven) in water 4 wt % sugar beet pectin solution in water 100 mM hydrogen peroxide 0.106 mg/ml (specific activity=6.10 exp 5 units per mg at pH 6) ARP (peroxidase from Arthromyces Ramosus.

Horseradish peroxidase (HRP) stock solution 0.6 mg/ml specific activity 3.2 exp 4 units per mg.

Experiments were performed in glass 10 ml tubes. An ultra-turrax was used at the highest speed. All the components, except for the enzyme, were mixed and briefly (1-2 seconds) submitted to high shear with a Turrax™ mixer at the highest speed. Then the enzyme was added (during shear). When the foam had been formed (after a few seconds), the shear treatment was stopped so that the enzyme could fix the foam.

TABLE 1

| | composition examples 1-2 | | | | |
|---|---|---|---|---|---|
| Sample no. | Water (µl) | 4% pectin solution (µl) | 12.5% egg white solution (µl) | 100 mM hydrogen peroxide (µl) | ARP (µl) |
| 1 | 1000 | 1000 | — | 20 | 40 |
| 2 | 680 | 1000 | 320 | 20 | 40 |

Results Examples 1-2:

TABLE 2

| sample no. | Freeze-thaw stable | Visual characteristics | Storage stability at 20° C. |
|---|---|---|---|
| 1 | yes | White foam | good |
| 2 | yes | White foam | good |

Example 3-7

Materials:
Sunflower oil
4% sugar beet pectin solution, sugar beet GENU pectin type BETA from CP Kelco (Denmark) product info number 1005-19, batch no 02995.
100 mM hydrogen peroxide
0.106 mg/ml ($2.10^4$ ABTS units at pH 6) ARP (peroxidase from *Arthromyces ramosus* stock solution 0.106 mg/ml, activity 2.10e4 ABTS units per ml).

Process

Oil-in-water: pectin, water and hydrogen peroxide were mixed and then submitted to high shear with a Turrax™ mixer at the highest speed. During shear treatment the oil was added slowly. When all the oil had been added, ARP was added.

Water-in-oil: pectin, water and hydrogen peroxide were mixed separately (water phase). The oil phase was submitted to high shear with a Turrax™ mixer at the highest speed and the water phase was added slowly. When the complete water phase was added, ARP was added to the emulsion.

Experiments were performed in small glass jars (~10 ml). The ultra-turrax™ (Janke & Kunkel, IBA labortechniek) T25, 24000 rpm as used at the highest speed.

TABLE 3

| Sample no. | water (μl) | 4% pectin (μl) | sunflower oil (μl) | 100 mM hydrogen peroxide (μl) | ARP (μl) | HRP (μl) |
|---|---|---|---|---|---|---|
| 3 | 1600 | 2000 | 400 | 40 | 80 | — |
| 4 | 1600 | 2000 | 400 | 40 | — | 14 |
| 5 | 1200 | 2000 | 800 | 40 | 80 | — |
| 6 | 400 | 2000 | 1600 | 40 | 80 | — |
| 7 | 400 | 2000 | 1600 | 40 | 80 | — |

Example number 7 resulted in a water in oil emulsion, the others were oil in water emulsions.

Results:

TABLE 4

| sample no. | % oil | Visible characteristics of product | Stability (after 3 days at 20° C.) |
|---|---|---|---|
| 3 | 10 | white, firm | little water release |
| 4 | 10 | white, firm | see 3 |
| 5 | 20 | white, firm | little water release but less than in 3 and 4 |
| 6 | 40 | white, firm | no oil release |
| 7 | 40 | white, firm | no oil release |

The firm white structure that was formed looked creamy, was tasteless and felt soft in the mouth.

Examples 8-9

The procedure of example 1 and 2 was used, with the ingredient composition as outlined below. In stead of an ultraturrax, a Hobart™ mixer at maximum speed (3) was used for foam formation before oxidation. The Hobart™ mixer used was a model N5D at maximum speed (1425 rpm) equipped with a wired whisk (B flat beater). ARP was added immediately when a foam had been formed after which mixing was continued for about 15 seconds. The time of shear treatment in the Hobart™ mixer was 5 minutes for example 8 and 9.

TABLE 5

| | composition examples 8 and 9 | | | | |
|---|---|---|---|---|---|
| Sample no. | Water (ml) | 4% pectin solution (ml) | 12.5% egg white solution (ml) | 1 M hydrogen peroxide (ml) | ARP (ml) |
| 8 | 125 | 125 | — | 0.25 | 5 |
| 9 | 85 | 125 | 40 | 0.25 | 5 |

Results Examples 8 and 9

TABLE 6

| sample no. | Freeze-thaw stable | SV before thawing | hardness value at 25 °C. | Visual characteristics | Water release after 24 hours |
|---|---|---|---|---|---|
| 8 | yes | 0.81 g/ml | 25.5 | White foam | 0.13 ml/g |
| 9 | yes | 0.14 g/ml | 14 | White foam | 0.16 ml/g |

It was concluded that in the presence of some egg white, a higher specific volume can be obtained. However these products are less stable and less firm although they still show the desired firmness and stability.

Example 10

0.2 g sodiumbicarbonate and 0.26 g disodiumpyrophosphate were added to 10 ml 4% sugar beet pectin (the same as described in ex. 3-7) solution under stirring with a magnetic stirrer bar. Immediately after the salts were added, 80 μl polyporus pincitus laccase was added (6.6 mg/ml, 22 Units/mg) to obtain oxidising of the ferulic acid groups of pectin.

The resulting product was a stable foam.

Comparative Examples (Not According to the Invention)

Comparative Examples A-C Composition

TABLE 7

| Sample no. | Water (μl) | 4% pectin (μl) | 12.5% egg white (μl) | 100 mM hydrogen peroxide (μl) | ARP (μl) |
|---|---|---|---|---|---|
| A | — | — | 2000 | — | — |
| B | 1680 | — | 320 | — | — |
| C | 680 | 1000 | 320 | — | — |

Comparative Example A-C Results

TABLE 8

| sample no. | Freeze-thaw stable | Storage stability at 20° C. |
|---|---|---|
| A | no | Instable |
| B | No | Instable |
| C | No | instable |

After 5 minutes at room temperature in samples A, B, C, a liquid layer was formed under the foam. After about 30 minutes this effect had slightly increased.

Therefore it is concluded that the lack of fixing of the foam structure by oxidation, leads to instable products, not fulfilling the requirements of the invention.

Comparative Example D-F

TABLE 9

| Sample no. | water (μl) | 4% pectin (μl) | sunflower oil (μl) | 100 mM hydrogen peroxide (μl) | ARP (μl) | HRP (μl) |
|---|---|---|---|---|---|---|
| D | 1600 | 2000 | 400 | 40 | — | — |
| E | 1200 | 2000 | 800 | 40 | — | — |
| | — | 2000 | 2000 | 40 | 80 | — |

Results Comparative Example D-F

TABLE 10

| sample no. | % pectin | % oil | result | Stability (after 3 days) |
|---|---|---|---|---|
| D | 2% | 10 | white, fluid | |
| E | 2% | 20 | white, fluid | complete phase separation |
| F | 2% | 50 | white, fluid | complete phase separation |

On the basis of these results it was concluded that high amounts of oil outside the claimed range, leads to instable products. Furthermore if no oxidant is present, there is either no foam formation or the formed foam is instable.

Comparative Example G, H, I

The procedure of comparative example A and B was used, with the ingredient composition as outlined below. In stead of an ultraturrax, a Hobart mixer at maximum speed (3) was used for foam formation before oxidation.

TABLE 11 composition comparative examples G, H, I

| Sample no. | Water (ml) | 4% pectin solution (ml) | 12.5% egg white solution (ml) | 1 M hydrogen peroxide (ml) |
|---|---|---|---|---|
| G | 210 | 125 | — | 0.25 |
| H | 85 | 125 | 40 | — |
| I | — | — | 125 | — |

Results Comparative Examples G, H, I

TABLE 12

| sample no. | Freeze-thaw stable | SV before thawing | hardness value at 25° C. (g) | Water release after 24 hours (ml/g) |
|---|---|---|---|---|
| G | No | 0.11 g/ml | 26.5 | 0.93 |
| H | No | 0.088 g/ml | 15.5 | 0.82 |
| I | no | 0.073 | 7 | 0.95 |

On the basis of these experiments it was concluded that the absence of oxidant or the use of a not powerful oxidant such as hydrogenperoxide as such, leads to the formation of products which are not freeze-thaw stable.

Example 11

The formulation shown in Table 13 was prepared. This base mix was then aerated (a) with the cross-linking of the pectin and (b) without the cross-linking of the pectin (comparative example). The aerated mixes were then frozen, and the improved temperature stability of the ice cream products was demonstrated using a meltdown test.

TABLE 13

Formulation of the base mix

| Ingredient | wt. % |
|---|---|
| Skimmed Milk Powder (Sunsheaf, Ca. 35% protein) | 7.4 |
| Whey Powder ("Espiron 300", DMV Int., Ca. 30% protein) | 2.6 |
| Sucrose (Tate and Lyle) | 15.6 |
| Coconut Oil ("HARDKO", Loders Croklaan) | 12 |
| Saturated Mono-/di- glycerides ("Admul MG40-04, Quest Int.) | 0.39 |
| Vanilla Flavour (Quest Int.) | 0.05 |
| β-carotene (Roche) | 0.01 |
| Sugar Beet Pectin ("Genu ® Beta pectin", CP Kelco) | 2 |
| Water | to 100% |

Mix Preparation

The pre-mix is the unhomogenised, unpasteurised mixture of ingredients. 40 kg of pre-mix was made up by adding milk powders, sugars and stabiliser to water at 55° C. In these formulations, emulsifiers were dissolved in molten fat before the mixture was blended with the aqueous ingredients.

The pre-mix was then heated to 82° C. with a plate heat exchanger, followed by homogenisation with a single stage valve homogeniser (APV Crepaco Homogeniser F-8831 3DDL) at 140 bar pressure. The pre-mix was then pasteurized at this temperature for 25 seconds. The mix was cooled to 5° C. with a plate heat exchanger, and then collected in a 50 kg stainless steel churn, and stored at 2° C.

Aeration of the Mix

From this base mix (formulation shown in Table 13), three aerated mixes were produced. 4 kg batches of mix were aerated using a Hobart mixer set at speed setting 3. The mixes were all aerated to approximately 100% overrun. To achieve 100% OR took approximately 8 minutes of continuous whipping. Cross-linking agents were added as follows:

Mix 1. With no cross-linking of the pectin during aeration (i.e. no addition of enzyme and hydrogen peroxide).

Mix 2. Where the pectin was cross-linked during aeration by the addition of 0.175 wt. % Biobake Wheat (peroxidase) to the mix, followed by 0.2% (w/v) of 1 mol $dm^{-3}$ hydrogen peroxide before aeration began.

Mix 3. Where the pectin was cross-linked after aeration by the addition of of 0.175 wt. % Biobake Wheat (peroxidase) to the mix, followed by 0.2% (w/v) of 1 mol $dm^{-3}$ hydrogen peroxide to the aerated mix. Further mixing (20 s) was used to incorporate the ingredients evenly.

(Biobake Wheat is an enzyme preparation from Quest International that contains soy bean peroxidase with an activity of 2000 units per g.)

Following aeration, the products were collected in 500 mL wax-coated cartons, and frozen at −25° C.

Experimental Procedure for Meltdown Tests

Tests were performed on a stainless steel wire mesh grid having a size of 25×25 cm, with 5 mm holes, 1 mm thick wire. Underneath the grid was disposed a collecting vessel (of large enough volume to collect the entire sample tested) and balances for weighing the material collected in the vessel. The balances are connected to a data logging system to record the mass collected The grids were placed in a meltdown cabinet set at a constant temperature environment 37° C. and which was capable of holding up to 12 of these grids simultaneously. Trays of water were placed within the cabinet to increase humidity and prevent any samples placed therein from drying.

Before placement in the cabinet the ice cream samples were equilibrated in a freezer at −25° C., and then weighed on a zeroed balance. They were then placed on the mesh grid and were arranged randomly over the available positions in the meltdown cabinet. Once all samples were in place, the data logging system measured the amount of collected material every minute over a 240 minute time period.

From the mass of the sample collected over this period, the percentage mass loss of the samples is calculated using the following formula.

$$\% \ MassLoss = \frac{M_t - M_0}{F} \times 100$$

wherein;

$M_t$=mass recorded (gram) at time t minute
$M_0$=mass recorded (gram) at start of analysis, t=0 minute
F=Initial mass of product (gram)

The % mass loss (% ML) for two samples of each formulation was averaged. From these data, the initiation time ($t^{4\%}$) for each sample of formulation was calculated. This is defined by the time that elapses before a percentage mass loss of 4% is achieved.

Results of the Meltdown Test

Initiation times for the mixes, and mass loss after 120 and 240 minutes are summarised in Table 14.

TABLE 14

Initiation time and mass loss data for the three ice cream products.

| Mix | Initiation time ($t^{4\%}$)/ minute | Mass loss after 120 minutes/% | Mass loss after 240 minutes/% |
|---|---|---|---|
| 1 | 12 | 93 | 92 |
| 2 | — | 0 | 0 |
| 3 | — | 0 | 0 |

From these data, it is concluded that the cross-linking of the pectin (both during and after aeration) leads to a significantly more stable foam compared to the same formulation containing pectin which is not cross-linked. Mix 1, where no cross-linking of the pectin occurs, shows rapid meltdown behaviour. Mixes 2 and 3, where cross-linking of the pectin does take place, show no appreciable meltdown whatsoever over the 240 minute time period.

The presence of a low amount of vanillin, in combination with the oil, did not negatively influence the final product.

The invention claimed is:

1. Process for the preparation of a frozen confection comprising the steps of:
    a) preparing an aqueous mixture of ingredients of the frozen confection and a ferulyolated compound dissolved in water, said ingredients of the frozen confection comprising sweetener, flavor components and optionally protein, fat, thickeners, emulsifiers, preservatives, and color components,
    b) incorporating a gas phase in the mixture formed in step a) to form a foam having an overrun of from 30% to 150%,
    c) mixing the foam formed in step b) with an oxidant capable of oxidation of the ferulic acid groups in the ferulyolated compound,
    d) freezing the resulting foam formed in step c) at a temperature below minus 4° C.,
    wherein the ferulyated compound in step a) contains a majority of ferulic acid groups that are not oxidised before the gas phase is incorporated in step b), and wherein in step c) ferulic acid groups are linked by oxidation carried out either simultaneously or after the incorporation of gas in step b).

2. Process according to claim 1 wherein the gas phase is incorporated by a method selected from the group consisting of subjecting the mixture to high shear treatment, addition of a leavening system under conditions where leavening takes place, and addition of an enzymatic system which leads to gas formation.

3. Process according to claim 1 wherein the oxidant is an enzyme or enzymatic system.

4. Process according to claim 1 wherein the ferulic acid groups of the ferulyated compound in step a) are at most 10% oxidized before the gas phase is incorporated in step b).

5. Process according to claim 1 wherein in step c) ferulic acid groups are linked by oxidation carried out after the incorporation of gas in step b).

6. A frozen confection made by the process according to claim 1 comprising a dispersed gas phase in a liquid phase to form a foamed product, said liquid phase comprising water, an oxidized ferulyolated compound, sweetener, flavor components and optionally protein, fat, thickeners, emulsifiers, preservatives, and color components, wherein the foamed product when stored at a temperature of at or below −20° C. for a period of at least 2 hours and subsequently thawed at about 25° C. will maintain a specific volume which is 70% to 100% of its initial specific volume before it was stored at or below −20° C.

7. Frozen confection according to claim 6 wherein the liquid phase comprises water in an amount of at least 20 wt % on total weight of the liquid phase.

8. Frozen confection according to claim 6 which comprises protein in an amount from 0.1 to 20 wt % on total weight of the liquid phase.

9. Frozen confection according to claim 6 which comprises up to 60 wt % oil on total weight of the liquid phase.

10. Frozen confection according to claim 6 having a specific volume of from 0.01 to 0.9 g/ml.

11. Frozen confection according to claim 6 wherein the ferulyolated compound is a pectin.

12. Frozen confection according to claim 11 wherein the ferulyolated compound is sugar beet pectin.

* * * * *